United States Patent [19]
Hsu

[11] Patent Number: 4,596,089
[45] Date of Patent: Jun. 24, 1986

[54] G-BANDING OF PLANT CHROMOSOMES

[75] Inventor: Tao-Chiuh Hsu, Harris, Tex.

[73] Assignee: The Board of Regents, The University of Texas System, Austin, Tex.

[21] Appl. No.: 553,629

[22] Filed: Nov. 21, 1983

[51] Int. Cl.$^4$ .............................................. A01G 1/00
[52] U.S. Cl. .......................................... 47/58; 424/3; 435/6; 435/317
[58] Field of Search .................... 47/58; 424/3; 435/6, 435/317

[56] References Cited
PUBLICATIONS

93 Chemical Abstracts, 40643p (1980).
Sumner, A. T., "Dye Binding Mechanisms in G-Banding of Chromosomes", *Journal of Microscopy*, vol. 119, pt. 3 (1980), pp. 397–406.
Taniguchi, K. et al., "Banding Techniques for Plant Chromosomes", Scibo, vol. 9, No. 4 (1977), pp. 126–131.
Schweizer, D., "DAPI Fluorescence of Plant Chromosomes Prestained with Antinomycin D", *Exp. Cell. Res.*, vol. 102 (1976), pp. 408–413.
Hsu, T. C. et al., "Induction of Chromosome Crossbanding by Treating Cells with Chemical Agents Before Fixation", *ExpH. Cell Res.*, vol. 79 (1973), pp. 484–487.

*Primary Examiner*—Robert E. Bagwill
*Attorney, Agent, or Firm*—Arnold, White & Durkee

[57] ABSTRACT

A method for the staining of the chromosomal material of plant cells so as to induce G-Bands, useful in plant genetic studies such as hydridization. G-Banding is induced by contacting living plant cells, such as those of plants of the family Gramineae, with actinomycin D, N-methyl-N'-nitroguanidine or ethidium bromide. More particularly, plant cells are treated with AMD and colchicine before fixation, prepared for viewing through a microscope by staining and then mounted on a glass slide.

7 Claims, 2 Drawing Figures

G-BANDING OF PLANT CHROMOSOMES

BACKGROUND OF THE INVENTION

The present invention relates to the staining of chromosomal material, and more particularly to the formation of G-Bands in plant chromosomes.

Staining of chromatin for microscopic examination has long been used as a method for monitoring chromosomal changes or abnormalities in both plants and animals. Several techniques are available, each of which results in a specific pattern of bands of color deposition in the chromosomes. Among the best known banding techniques are those which induce the formation of C-Bands, G-Bands, and R-Bands. The term "C-Bands" is used to describe the light and dark bands which appear on the chromosomes when viewed through a microscope which are the result of treatment of the cells with certain known staining processes. The locations of these light and dark bands are specific for each specie from which the cells are taken.

G-Bands are much finer than C-Bands, have specific widths, run longitudinally along the chromosomes and have specific intervals between bands. R-Bands are the reverse of G-Bands: dark G-Bands appear as light R-Bands and light G-Bands appear as dark R-Bands.

G-Banding (and its equivalent, R-Banding) is a particularly useful banding technique which was originally described by M. Seabright, Lancet ii, 971 (1971) for which there have been many technical improvements, especially prophase chromosome banding (see J. J. Yunis, 191 Science 1268 (1976)). For instance, G-Bands can be used by medical geneticists to identify cancer and many congenital abnormalities in humans. Although the techniques used to induce G-Bands in chromosomes were not equally successful in all animal species, G-Banding became a widely used technique for the monitoring of chromosomal changes in vertebrate species. If two chromosomes were to exchange segments during cell division (mitosis), C-Banding would not detect the exchange whereas G- or R-Banding techniques can be used to easily monitor such changes. The use of G-Banding has contributed significantly to advancements in human and mammalian cytogenetics.

However, all previous attempts to induce the formation of G-Bands in the chromosomes of plant cells have been unsuccessful, resulting instead in the formation of C-Bands. For instance, K. Taniguchi and R. Tanaka, 9 Scibo 126 (1977) report a procedure for induction of C-Bands and J. K. S. Sachan and R. Tanaka, 51 Jap. J. Genet. 139 (1976), E. J. Ward, 22 Can. J. Genet. Cytol. 61 (1980) and C. Chow and E. N. Larter, 23 Can. J. Genet. Cytol. 255 (1981) all report attempts to induce G-Bands in plant chromosomes which resulted in C-Bands. Additionally, it has been suggested that it is not possible to induce G-Banding in plant chromosomes (see J. Greilhuber, 50 Theor. Appl. Genet. 121 (1977)).

In general, currently available banding techniques for staining of both plant and animal cells utilize post-fixation treatments. In accordance with such techniques, the cells are first fixed by interrupting the dynamic processes of the cell as quickly as possible and stabilizing the chemical structures of the cell with a minimum of change. Following fixation, slides are prepared for viewing through the microscope. A variety of chemicals such as urea, potassium permanganate and trypsin may be used to induce post-fixation G-Band formation in air-dried cytological preparations at plant cells.

G-Band formation can also be induced by treating growing cells with chemicals, such as actinomycin D (AMD) which binds with the guanine residues of bihelical DNA (D. Schweizer, 102 Exp. Cell Res. 408 (1978)), before fixation. Attention is called to an article by T. C. Hsu, S. Pathak and D. A. Shafer (78 Exp. Cell Res. 484 (1973)) which discloses the use of AMD, ethidium bromide, Nogalamycin and azure B to induce G- or R-Bands in mammalian chromosomes by prefixation treatment. In general, R-Bands were induced by the same procedure used to induce G-Band formation with the additional post-fixation step of heating the cells in a phosphate buffer solution at 90° C. Although AMD gave excellent results, this technique was not as popular as post-fixation treatments because AMD is highly toxic to living cells. As a result of the high toxicity, when cell cultures are treated with AMD for a few hours, they yield very few actively dividing cells for subsequent staining upon harvest. Treatment of the actively dividing cells with colchicine, or similar agents, creates the potential for a high yield of cells in early mitotic phases because colchicine arrests the mitotic process prior to cell division. Because colchicine treatment makes available a large number of cells that are in the process of dividing, the fact that treatment with AMD is toxic to the cells has little effect on the number of cells available for subsequent pre-fixation treatment to induce G-Bands.

This invention overcomes many of the limitations discussed above and provides, for the first time, a process for the staining of the chromosomes of plant cells which results in the formation of G-Bands.

Using the method of the present invention, plant chromosomes may be banded in patterns which are characteristic for each plant specie. These characteristic banding patterns are of considerable significance to plant breeders and geneticists who monitor the chromosomal complement of the plant specie, for instance, in hybridization studies. In particular, the banding patterns allow the identification of chromosomes and chromosome segments as they might have been exchanged or distributed upon segregation of the chromosomes during mitosis or meiosis.

SUMMARY OF THE INVENTION

In its broadest scope, the present invention provides a method for inducing G-Bands in plant chromosomes prior to fixation by contacting plant cells with an amount of a G-Band inducing agent selected from the group consisting of actinomycin D, ethidium bromide or N-methyl-N'-nitroguanidine.

In accordance with the present invention, one embodiment involves contacting living plant cells with an agent to arrest mitosis and a G-Band inducing effective amount of actinomycin D, ethidium bromide or N-methyl-N'-nitroguanidine or solutions thereof. The agent used to arrest mitosis may, for example, be an aqueous solution of colchicine.

The cells are then contacted with an effective amount of an appropriate agent to effect the unraveling of the chromosomes of the cells. For example, Ohnuki's solution can be so utilized. The cells are then fixed, contacted with an effective amount of an agent to effect the disruption of their cellular structure, and contacted with an agent for a time and in an amount effective to stain the chromosomes.

BRIEF DESCRIPTION OF THE DRAWINGS

FIG. 1(A) shows a conventional unbanded karyotype, FIG. 1(B) shows a conventional karyotype in which the chromosomes were stained according to the method of the present invention, and FIG. 1(C) shows a prometaphase karyotype of chromosomes stained according to the method of the present invention.

DETAILED DESCRIPTION OF THE INVENTION

The following procedures may be used for preparing banded chromosomes in the cells of monocotyledenous plants, particularly of the family Gramineae. Although the procedures provided induce bands in the somatic chromosomes of cells excised from the root-tips of maize (*Zea* mays) or any species selected from the genus Triticum (wheat), with appropriate modifications, they may be suitably utilized to induce bands in the chromosomes of cells of other representatives of the Gramineae family and from other parts of the plant. The preferred agent for the induction of G-Bands in the cells of plants of this family is actinomycin D (AMD), however, ethidium bromide and N-methyl-N'-nitroguanidine (MNNG) may also be utilized. In general, the bands which are induced by ethidium bromide and MNNG are not as distinct as those induced by AMD.

EXAMPLE I

Method for inducing G-Bands in somatic chromosomes of *Zea* mays

Commercially purchased popcorn seeds were soaked in tap water for one hour, then transferred onto wet filter paper in Petri dishes for three days.

Excised primary root-tips were pretreated with an aqueous, unbuffered AMD solution (70–75 ug/ml) at room temperature in the dark for one hour, then treated with aqueous, unbuffered colchicine (0.05% final concentration) for an additional hour. The root-tips were then treated with Ohnuki's solution (an equimolar 10:5:2 mixture of 0.055 M KCl, $NaNO_3$ and sodium acetate in water at room temperature for 1.5 to 2 hours.

The root-tips were then fixed in Carnoy's fixative (3 methanol:1 acetic acid) for 30 minutes at room temperature, and rinsed in running tap water for one hour. They were then softened for 1.5 hours at 37° C. in an aqueous solution of 6% cellulase (Sigma, E.C. No. 3.2.1.4) and 6% pectinase (Sigma, E.C. No. 3.2.1.15) and adjusted with HCl to a pH of between 4 and 5.

Root-tips were rinsed briefly in distilled water and re-fixed in Carnoy's fixative overnight at 4° C. They were then stained with a few drops of 2% aceto-orcein (Gurr's natural, London) on a clean slide, the slides were heated on a hot plate at 40°–45° C. for 10–16 minutes, then squashed and sealed.

Figure 2:
FIG. 2 shows a *Zea* mays cell in prophase with distinct crossbanding along the chromosomes resulting from treatment of the cell by the method of the present invention.
Figure 1:
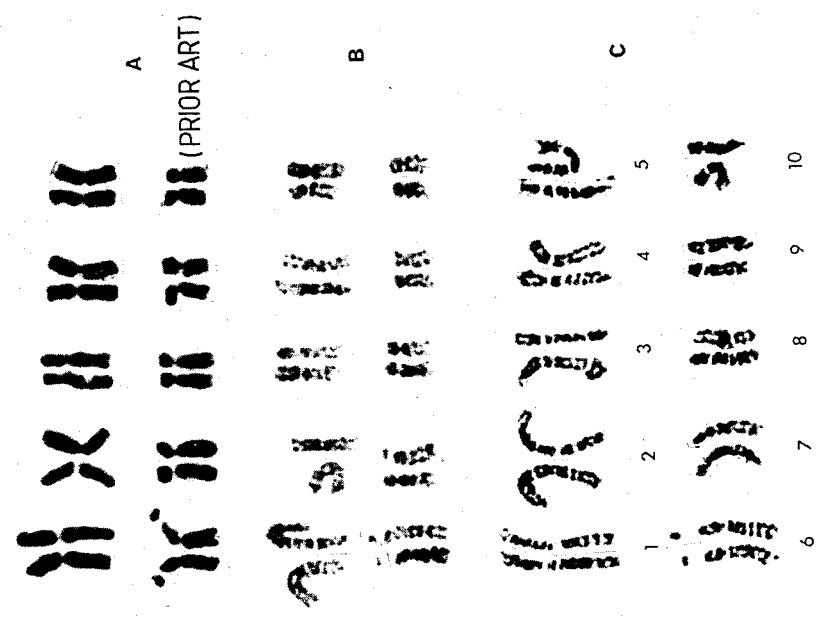
FIG. 1 shows three karyotypes of *Zea* mays chromosomes arranged according to Chen's system (see Chi-Chang Chen, 11 Can. J. Genet. Cytol. 752 (1969)).

Using the above-described method, chromosome crossbands can be observed in cells in both metaphase and prophase (FIGS. 1 and 2, respectively). FIG. 1(A) shows a conventional, unbanded karyotype of *Zea* mays as can be prepared by any of a number of methods available in the prior art. By comparison, FIG. 1(B) shows a banded karyotype of chromosomes stained according to the method of the above-described example FIG. 1(C) shows a karyotype of chromosomes stained according to the method of the above-described example taken from a cell in an earlier metaphase stage, prometaphase, in which the chromosomes are not as contracted. As can be seen in both FIG. 1(B) and FIG. 1(C), homologous chromosomes exhibit similar banding patterns. FIG. 2 shows a *Zea* mays cell stained according to the above-described example in prophase, with distinct crossbands clearly visible in all chromosomal material.

EXAMPLE II

Method for inducing G-Bands in somatic chromosomes of Triticum

Induction of G-Bands in the chromosomes of wheat (Triticum) was accomplished using essentially the same method as described in Example I for *Zea* mays.

EXAMPLE III

Method for inducing G-Bands in somatic chromosomes of *Zea* mays utilizing ethidium bromide Induction of G-Bands in the chromosomes of the somatic cells of *Zea* mays may also be accomplished utilizing ethidium bromide in place of AMD. Cells were contacted with ethidium bromide in aqueous solution in concentration of approximately 350 ug/ml, but in all other respects, the method was essentially similar to the method as described in Example I.

EXAMPLE IV

Method for inducing G-Bands in somatic chromosomes of *Zea* mays utilizing MNNG

Induction of G-Bands in the chromosomes of the somatic cells of *Zea* mays may also be accomplished utilizing MNNG in aqueous solution in concentration of approximately 500 ug/ml, but in all other respects, the method was essentially similar to the method as described in Example I.

It is understood that the invention and the advantages and opportunities presented by it will be recognized from the above description, which merely describes several preferred methods of the invention. It is apparent that many changes in the materials, methods and amounts of materials utilized are possible. In fact, with certain types of plant cells which possess chromosomes which are markedly larger or smaller than those of maize or wheat, variations may be necessary.

For example, it may be necessary to vary the length of the exposure to AMD or to use a different concentration of AMD. A concentration of 3.5 ug/ml AMD has been found to be ineffective for induction of G-Bands of good resolution in maize chromosomes, but depending on the plant cell, an AMD concentration in that range or as high as approximately 100 ug/ml may be necessary. Further, similar results may be obtained by exposing cells to AMD and colchicine simultaneously.

Similarly, the use of other agents for fixation, inducement of band formation or staining is possible. With the regimen detailed in the above-described examples, the best results were obtained when AMD was used to induce band formation. As noted, both ethidium bromide and MNNG will induce band formation in *Zea* mays, but the bands are of poorer quality than those induced by AMD when the above-detailed regimen is used. It may be that changes in that regimen will improve the quality of the bands formed when either ethidium bromide or MNNG are used in place of AMD.

Synthetic orcein, carmine, Geimsa and lacto-proprionic orcein have been tried with varying results, and it may be that modifications to the above-described regimen will improve the quality of the bands formed when these stains are used.

It is also possible to induce band formation in plant chromosomes in air-dried rather than squash preparations. In squash preparations, the use of other agents for hydrolysis of the cells is well known. The use of cellulase and pectinase is preferred because hydrolysis with acids such as hydrochloric or acetic acid may damage the chromosomes. However, under properly controlled conditions, such acids could be used to effectively hydrolyze the cells. Likewise, agents other than Ohnuki's solution, for example, a mixture of 1 M NaCl and 0.1 M sodium citrate (see V. C. Lavania, 47 Curr. Sci. 255 (1978)), may be used to unravel the chromosomes and thereby promote the formation of the bands.

It will be apparent to those skilled in the art who have the benefit of this disclosure that such modifications are within the spirit and scope of the present invention and that the present invention is not limited by the examples discussed above, but rather only by the lawful scope of the appended claims.

What is claimed is:

1. A method for inducing G-Bands in chromosomes of plants selected from the family Gramineae which comprises contacting a living cell from such a plant with a G-Band inducing effective amount of actinomycin D, ethidium bromide or N-methyl-N'-nitroguanidine and solutions thereof prior to fixation of said plant cell.

2. A method for inducing G-Bands in Zea mays chromosomes which comprises contacting a living Zea mays cell with a G-Band inducing effective amount of actinomycin D, ethidium bromide or N-methyl-N'-nitroguanidine and solutions thereof prior to fixation of said plant cell.

3. A method for inducing G-Bands in chromosomes of plants selected from the genus Triticum which comprises contacting a living cell from such a plant with a G-Band inducing effective amount of actinomycin D, ethidium bromide or N-methyl-N'-nitroguanidine and solutions thereof prior to fixation of said plant cell.

4. A method for inducing G-Bands in the chromosomes of cells of plants selected from the family Gramineae, which comprises:
contacting said cells with an agent to arrest mitosis and a G-Band inducing effective amount of actionomycin D, ethidium bromide or MNNG or solutions thereof;
contacting said cells with an effective amount of an agent appropriate to effect the unraveling of the chromosomes of said cells;
fixing said cells;
contacting said cells with an effective amount of an agent to effect the disruption of the cellular structure of said cells; and
contacting said cells with an agent for a time and in an amount effective to stain said chromosomes.

5. A method for inducing G-Bands in the chromosomes of Zea mays cells, which comprises:
contacting said cells with an agent to arrest mitosis and a G-Band inducing effective amount of actinomycin D, ethidium bromide or MNNG or solutions thereof;
contacting said cells with an effective amount of an agent appropriate to effect the unraveling of the chromosomes of said cells;
fixing said cells;
contacting said cells with an effective amount of an agent to effect the disruption of the cellular strucuture of said cells; and
contacting said cells with an agent for a time and in an amount effective to stain said chromosomes.

6. A method for inducing G-Bands in the chromosomes of cells of plants selected from the genus Triticum, which comprises:
contacting said cells with an agent to arrest mitosis and a G-Band inducing effective amount of actinomycin D, ethidium bromide or MNNG or solutions thereof;
contacting said cells with an effective amount of an agent appropriate to effect the unraveling of the chromosomes of said cells;
fixing said cells;
contacting said cells with an effective amount of an agent to effect the disruption of the cellular structure of said cells; and
contacting said cells with an agent for a time and in an amount effective to stain said chromosomes.

7. G-banded plant chromosomes prepared according to claim 1, 2, 3, 4, 5, or 6.

* * * * *

UNITED STATES PATENT AND TRADEMARK OFFICE
CERTIFICATE OF CORRECTION

PATENT NO. : 4,596,089

DATED : June 24, 1986

INVENTOR(S) : Tao-Chiuh Hsu

It is certified that error appears in the above—identified patent and that said Letters Patent is hereby corrected as shown below:

In the ABSTRACT, line 3, change "hydridization" to --hybridization--.

Column 3, lines 3, 12, 24, 38, 66, the word "mays" should appear in italics.

line 25, the word "Triticum" should appear in italics.

Column 4, lines 9, 19, 23, 26, 35, 38, 67, the word "mays" should appear in italics.

line 18, the word "Triticum" should appear in italics.

Column 5, lines 39, 40, the word "mays" should appear in italics.

line 46, the word "Triticum" should appear in italics.

Column 6, lines 5 and 6, change "ac-tionomycin" to --ac-tinomycin--.

line 18, the word "mays" should appear in italics.

lines 28 and 29, change "strucu-ture" to --struc-ture--.

UNITED STATES PATENT AND TRADEMARK OFFICE
CERTIFICATE OF CORRECTION

PATENT NO. : 4,596,089

DATED : June 24, 1986

INVENTOR(S) : Tao-Chiuh Hsu

It is certified that error appears in the above-identified patent and that said Letters Patent is hereby corrected as shown below:

Column 6, lines 33 and 34, the word "Triti-cum" should appear in italics.

Signed and Sealed this

Twenty-eighth Day of October, 1986

[SEAL]

*Attest:*

DONALD J. QUIGG

*Attesting Officer*  *Commissioner of Patents and Trademarks*